(12) United States Patent
Aoki

(10) Patent No.: US 9,029,472 B2
(45) Date of Patent: May 12, 2015

(54) GEL COMPOSITION AND A USE THEREOF

(71) Applicant: Shin-Etsu Chemical Co., Ltd., Tokyo (JP)

(72) Inventor: Shunji Aoki, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 14/282,612

(22) Filed: May 20, 2014

(65) Prior Publication Data

US 2014/0356614 A1    Dec. 4, 2014

(30) Foreign Application Priority Data

May 30, 2013    (JP) ................................. 2013-114645

(51) Int. Cl.

| | | |
|---|---|---|
| C08L 83/04 | (2006.01) | |
| C09D 5/16 | (2006.01) | |
| C07F 7/18 | (2006.01) | |
| C04B 41/00 | (2006.01) | |
| C04B 41/49 | (2006.01) | |
| C09K 3/18 | (2006.01) | |
| C04B 41/64 | (2006.01) | |
| C08K 5/098 | (2006.01) | |
| C09D 183/04 | (2006.01) | |
| C08K 5/5419 | (2006.01) | |
| C09D 7/12 | (2006.01) | |
| C09D 183/06 | (2006.01) | |

(52) U.S. Cl.
CPC ............ *C09D 5/1675* (2013.01); *C07F 7/1836* (2013.01); *C04B 41/009* (2013.01); *C04B 41/4922* (2013.01); *C09K 3/18* (2013.01); *C04B 41/64* (2013.01); *C08K 5/098* (2013.01); *C09D 183/04* (2013.01); *C08K 5/5419* (2013.01); *C09D 5/165* (2013.01); *C09D 7/1233* (2013.01); *C09D 183/06* (2013.01)

(58) Field of Classification Search
CPC .... C08K 5/5419; C08K 5/098; C07F 7/1836; C09D 5/1675; C09D 183/04; C04B 1/009

USPC .................................. 524/858, 700; 428/447
See application file for complete search history.

(56) References Cited

U.S. PATENT DOCUMENTS

| | | | |
|---|---|---|---|
| 4,648,904 A | 3/1987 | DePasquale et al. | |
| 5,746,810 A | 5/1998 | Suzuki | |
| 5,962,585 A | 10/1999 | Mayer et al. | |
| 6,063,872 A * | 5/2000 | Nichols et al. ................ | 525/241 |

FOREIGN PATENT DOCUMENTS

| | | |
|---|---|---|
| JP | A-62-197369 | 9/1987 |
| JP | A-4-111979 | 4/1992 |
| JP | A-6-313167 | 11/1994 |
| JP | A-9-208938 | 8/1997 |
| JP | A-10-81824 | 3/1998 |
| JP | A-2004-315631 | 11/2004 |
| JP | A-2009-035704 | 2/2009 |
| JP | A-2009-155641 | 7/2009 |
| JP | A-2012-241100 | 12/2012 |
| WO | 0194487 A2 | 12/2001 |

OTHER PUBLICATIONS

Oct. 29, 2014 Extended European Search Report issued in Application No. 14169884.5.

* cited by examiner

*Primary Examiner* — Kuo-Liang Peng
(74) *Attorney, Agent, or Firm* — Oliff PLC

(57) ABSTRACT

The first aspect in the present invention provides a composition that includes (A) 100 parts by mass of an organoalkoxysilane represented by the following formula (1) and/or a compound obtained by partial hydrolysis and condensation of said organoalkoxysilane: R1aSi(OR2)4-a ... (1), (B) 0.3 to 20 parts by mass of an aluminum dicarboxylate represented by the following formula (2): (R3COO)2Al(OH) ... (2), and (C) 0.3 to 20 parts by mass of an aliphatic acid having 6 to 24 carbon atoms. The second aspect in the present invention provides a composition that includes components (A), (B) and (C) and further (D) 0.01 to 10 parts by mass of a dicarboxylic acid having 6 to 30 carbon atoms. Further, the present invention provides a method for making a porous material less water-absorptive by applying the composition to a surface of said porous material and a porous material modified by the method.

7 Claims, 1 Drawing Sheet

GEL COMPOSITION AND A USE THEREOF

CROSS REFERENCE

This application claims the benefits of Japanese Patent application Nos. 2013-114645 filed on May 30, 2013, and 2013-216427 filed on Oct. 17, 2013, the contents of which are incorporated by reference.

The present invention relates to a gel composition comprising an organoalkoxysilane. Further, the present invention relates to a use of the gel composition as an agent for making materials less water-absorptive, i.e. a water absorption-preventing agent.

BACKGROUND OF THE INVENTION

When inorganic porous materials for architectural or civil engineering are used in outdoor structures, they are exposed to rain and deteriorated by absorbed water, cause cracks due to freezing at low temperatures or damage by salt at seasides, and deterioration in appearance due to adhesion of fungi and algae. Therefore, measures to extend life spans of the structures are desired.

Examples of the inorganic porous materials include concrete, lightweight concrete, autoclaved lightweight aerated concrete (ALC), mortar, cement plates, plaster boards, calcium silicate plates, bricks, tiles and stones. In order to prevent deterioration of these porous materials, a water absorption-preventing agent is applied on and penetrates through a surface of the porous material to make the surface hydrophobic and prevent water and salts from penetrating through the surface of porous materials. Silicone compositions are known as a water absorption-preventing agent.

As the water absorption-preventing silicone agent, a solvent-borne water absorption-preventing agent comprising alkylalkoxysilane diluted with an organic solvent is known. However, a concentration of the alkylalkoxysilane and the viscosity are low in this water absorption-preventing agent. Therefore, a sufficient amount of the alkylalkoxysilane does not penetrate through a surface of a substrate by one-time application, so that a hydrophobic layer with a sufficient thickness is not formed on the surface of the substrate. Further, after applying the solvent-borne water absorption-preventing agent, VOCs, i.e. volatility organic compounds, evaporate from the organic solvent to deteriorate working environment and environmental problems. Therefore, a non-solvent type water absorption-preventing agent is desired in recent years.

Japanese Patent Application Laid-Open Nos. Sho62-197369, Hei-4-111979, Hei-6-313167, Hei-9-208938 and 2004-315631 describe that aqueous emulsion compositions comprising an alkylalkoxysilane, a surfactant or emulsifier and water are used as a water absorption-preventing agent. However, the surfactant remains on a surface of a substrate after applying the aqueous emulsion composition, so that the surface is not made sufficiently hydrophobic. Therefore, there are problems at the time of rain such that parts of the surface of the substrate have wet color to deteriorate the appearance and sufficient water repellency cannot be obtained.

Further, there is a problem such that the aqueous emulsion flows down when the aqueous emulsion is applied thickly on a surface of a substrate or applied on a vertical surface. Japanese Patent Application Laid-Open No. Hei-10-81824 describes that an aqueous cream, that is, water-containing paste composition, comprising an alkylalkoxysilane, an emulsifier and water is used as a water absorption-preventing agent. This water absorption-preventing agent is cream, so that it can be applied thickly on a surface of a substrate. However, in a short time after applying the agent, the emulsion state breaks and the alkylalkoxysilane having a low viscosity separates. Therefore, when the composition is applied on an inclined or vertical surface or an inverted surface of a substrate, dripping occurs, so that an effective component, alkylalkoxysilane, flows away and does not penetrate sufficiently through the surface.

Japanese Patent Application Laid-Open No. 2009-155641 describes a water absorption-preventing agent prepared by dispersing an alkylalkoxysilane and cyclodextrin in water. This water absorption-preventing agent leaves the cyclodextrin, which is a water soluble polymer, on a surface of a substrate, after applied and, therefore, the appearance of the substrate was deteriorated and sufficient water repellency cannot be obtained.

Japanese Patent Application Laid-Open No. 2009-35704 describes a water absorption-preventing agent comprising an alkylalkoxysilane and silica. The composition leaves white silica on a surface of a substrate, after applied, to damage appearance. Therefore, the silica is needed to be removed with a tool such as a brush. When the composition is applied on a large area, costs to remove the silica is large.

Japanese Patent Application Laid-Open No. 2012-241100 describes a water absorption-preventing agent comprising an alkylalkoxysilane and a thixotropic agent. Generally, commercial thixotropic agents are dissolved in an organic solvent such as xylene, mineral spirit, i.e. mineral turpentine, benzyl alcohol, ethanol and isopropanol. That is, the water absorption-preventing agent comprising the thixotropic agent contains an organic solvent. A thixotropic agent containing no organic solvent is powder and, therefore, it is difficult to disperse the thixotropic agent in an alkylalkoxysilane.

PRIOR LITERATURES

Patent Literatures

[Patent Literature 1] Japanese Patent Application Laid-Open No. Sho62-197369
[Patent Literature 2] Japanese Patent Application Laid-Open No. Hei-4-111979
[Patent Literature 3] Japanese Patent Application Laid-Open No. Hei-6-313167
[Patent Literature 4] Japanese Patent Application Laid-Open No. Hei-9-208938
[Patent Literature 5] Japanese Patent Application Laid-Open No. 2004-315631
[Patent Literature 6] Japanese Patent Application Laid-Open No. Hei-10-81824
[Patent Literature 7] Japanese Patent Application Laid-Open No. 2009-155641
[Patent Literature 8] Japanese Patent Application Laid-Open No. 2009-35704
[Patent Literature 9] Japanese Patent Application Laid-Open No. 2012-241100

SUMMARY OF THE INVENTION

One of the purposes of the present invention is to provide a composition which can make porous materials less water-absorptive. Specifically, the purpose of the present invention is to provide a water absorption-preventing agent which comprises an organoalkoxysilane, does not drip after applied, and provides water repellency to porous materials without deteriorating appearance, where the organoalkoxysilane penetrates deeply from a surface of porous materials.

Another purpose of the present invention is to provide a gel water absorption-preventing agent which cuts easily to have good workability in application, in addition to the aforesaid effects.

The present inventors have found that a combination of an aluminum dicarboxylate and an aliphatic acid enable a composition comprising an organoalkoxysilane to gel well. Further, after a gel composition comprising an aluminum dicarboxylate, an aliphatic acid and an organoalkoxysilane is applied on a surface of a substrate, the organoalkoxysilane does not separate from the composition and a viscosity of the gel composition does not decrease, either. Therefore, when the gel composition is applied on a surface of porous materials, the organoalkoxysilane is gradually absorbed in to pores of the porous materials while maintaining a viscosity of the gel state. Further, the present inventors have found that even when the composition is applied on an inclined or vertical surface, the gel composition does not drip and, thus, the organoalkoxysilane penetrates deeply through a surface of porous materials.

The first aspect of the present invention provides a composition comprising
(A) 100 parts by mass of an organoalkoxysilane represented by the following formula (1) and/or a compound obtained by partial hydrolysis and condensation of said organoalkoxysilane, $$R^1_a Si(OR^2)_{4-a} \qquad (1)$$

wherein $R^1$ is, independently of each other, a monovalent hydrocarbon group having 1 to 20 carbon atoms, $R^2$ is, independently of each other, a monovalent hydrocarbon group having 1 to 8 carbon atoms and a is an integer of 1, 2 or 3,
(B) 0.3 to 20 parts by mass of an aluminum dicarboxylate represented by the following formula (2):

$$(R^3COO)_2Al(OH) \qquad (2)$$

wherein $R^3$ is, independently of each other, a monovalent hydrocarbon group having 1 to 25 carbon atoms, and
(C) 0.3 to 20 parts by mass of an aliphatic acid having 6 to 24 carbon atoms.
The present invention further provides a use of the composition as a water absorption-preventing agent. This composition particularly has a gel state. In Particular, the composition in the first aspect does not comprise any dicarboxylic acid.

A gel of the aforesaid composition comprising an aluminum dicarboxylate, an aliphatic acid and an organoalkoxysilne is not easily cut and elongates long when it is scooped up from a vessel. The present inventors have made further research and found that by adding a dicarboxylic acid having 6 to 30 carbon atoms to the aforesaid composition in the first aspect, a gel of the composition cracks and cuts easily. Therefore, the gel is scooped up easily with a spatula from a vessel to be applied on porous materials. That is, the present inventors found that a dicarboxylic acid having 6 to 30 carbon atoms improves workability of the gel in applying it evenly, in addition to the effects in the aforesaid first aspect.

The second aspect of the present invention provides a composition comprising
(A) 100 parts by mass of an organoalkoxysilane represented by the following formula (1) and/or a compound obtained by partial hydrolysis and condensation of said organoalkoxysilane, $$R^1_a Si(OR^2)_{4-a} \qquad (1)$$

wherein $R^1$ is, independently of each other, a monovalent hydrocarbon group having 1 to 20 carbon atoms, $R^2$ is, independently of each other, a monovalent hydrocarbon group having 1 to 8 carbon atoms and a is an integer of 1, 2 or 3,
(B) 0.3 to 20 parts by mass of an aluminum dicarboxylate represented by the following formula (2):

$$(R^3COO)_2Al(OH) \qquad (2)$$

wherein $R^3$ is, independently of each other, a monovalent hydrocarbon group having 1 to 25 carbon atoms,
(C) 0.3 to 20 parts by mass of an aliphatic acid having 6 to 24 carbon atoms, and
(D) 0.01 to 10 parts by mass of a dicarboxylic acid having 6 to 30 carbon atoms.
The present invention further provides a use of the composition as a water absorption-preventing agent. This composition particularly has a gel state.

Further, the present invention provides a method for making a porous material less water-absorptive by applying the composition to a surface of said porous material, and a porous material modified by the method.

When the present compositions are applied on a surface of porous materials, an effective component, i.e. organoalkoxysilane, penetrates deeply from a surface of the material while the composition maintains a viscosity of a gel state and porous materials are made less water-absorptive, that is, provided well water repellency, without deteriorating the appearance. Therefore, the present compositions are useful as an agent for making materials less water-absorptive. Additionally, the present compositions can be used in a form of a solventless gel composition which comprises substantially neither water nor organic solvent. When the solventless gel composition is applied on a substrate, VOCs, i.e. volatility organic compounds, due to an organic solvent does not evaporate. Further, the composition in the second aspect has a good workability in applying it evenly on a surface of porous materials in addition to the aforesaid effects in the first aspect. The present compositions are particularly useful as an agent for making architectural or civil engineering inorganic porous materials less water-absorptive.

DETAILED DESCRIPTION OF THE INVENTION

Figure 1:
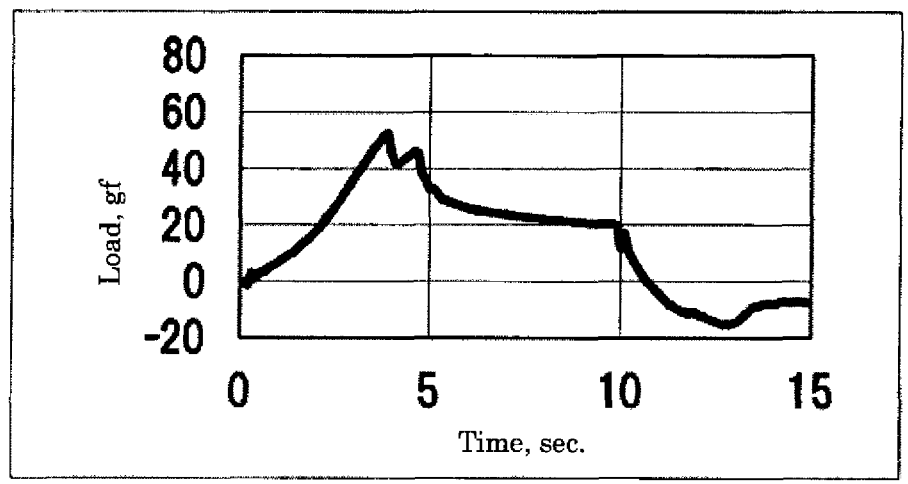
FIG. 1 is a load curve of the gel obtained in Example B10.

The present invention will be described below in detail.
Component (A) is an organoalkoxysilane represented by the following formula (1):

$$R^1_a Si(OR^2)_{4-a} \qquad (1)$$

and/or a compound obtained by partial hydrolysis and condensation of this organoalkoxysilane.

$R^1$ is, independently of each other, a monovalent hydrocarbon group having 1 to 20, preferably 3 to 20, further preferably 6 to 10 carbon atoms. Examples of the monovalent hydrocarbon group include alkyl groups such as a methyl group, an ethyl group, a propyl group, an isopropyl group, a butyl group, an isobutyl group, a t-butyl group, a pentyl group, an isopentyl group, a neopentyl group, a hexyl group, a cyclohexyl group, an octyl group, an isooctyl group, i.e. an alkyl group having 8 carbon atoms including 2,4,4-trimethylpentyl group, a decyl group, a dodecyl group and a norbornyl group; and alkenyl groups such as a vinyl group, an allyl group and a hexenyl group. $R^1$ may have a linear, cyclic or branched structure. Examples of $R^1$ further include aryl groups such as a phenyl group, aralkyl groups such as a styryl group, an amino group-containing alkyl groups such as a 3-aminopropyl group and N-(2-aminoethyl)-3-aminopropyl group, an epoxy group-containing alkyl groups such as a 3-glycidoxypropyl group and a fluorine atom-containing group such as a trifluoromethyl group and 3,3,3-trifluoropropyl group. Among these, an alkyl group having 3 or more carbon atoms is preferable, and an alkyl group having 6 to 10 carbon atoms is more preferable.

$R^2$ is, independently of each other, a monovalent hydrocarbon group having 1 to 8, preferably 1 to 6, more preferably 1 to 4 carbon atoms. Examples of $R^2$ include alkyl groups such as a methyl group, an ethyl group, a propyl group, an isopropyl group, a butyl group, a pentyl group and a hexyl group. Among these, a methyl group and an ethyl group are particularly preferable.

"a" is an integer of 1, 2 or 3, and particularly "a" is preferably 1.

Examples of the organoalkoxyxilane include trimethylmethoxysilane, trimethylethoxysilane, dimethyldimethoxysilane, dimethyldiethoxysilane, methyltrimethoxysilane, methyltriethoxysilane, ethyltrimethoxysilane, ethyltriethoxysilane, propyltrimethoxysilane, propyltriethoxysilane, butyltrimethoxysilane, butyltriethoxysilane, hexyltrimethoxysilane, hexyltriethoxysilane, octyltrimethoxysilane, octyltriethoxysilane, isooctyltrimethoxysilane, isooctyltriethoxysilane, 2-ethylhexyltrimethoxysilane, 2-ethylhexyltriethoxysilane, decyltrimethoxysilane, decyltriethoxysilane, phenyltrimethoxysilane, phenyltriethoxysilane, vinyltrimethoxysilane, vinyltriethoxysilane, N-(2-aminoethyl)-3-aminopropyltrimethoxysilane, N-(2-aminoethyl)-3-aminopropyltriethoxysilane, N-(2-aminoethyl)-3-aminopropylmethyldimethoxysilane, N-(2-aminoethyl)-3-aminopropylmethyldiethoxysilane, 3-glycidoxypropyltrimethoxysilane, 3-glycidoxypropyltriethoxysilane, 3-glycidoxypropylmethyldimethoxysilane, 3-glycidoxypropylmethyldiethoxysilane, trifluoromethyltrimethoxysilane and 3,3,3-trifluoropropyltrimethoxysilane. Among these, hexyltrimethoxysilane, hexyltriethoxysilane, octyltrimethoxysilane, octyltriethoxysilane, isooctyltrimethoxysilane, isooctyltriethoxysilane, methyltriethoxysilane, butyltriethoxysilane and propyltriethoxysilane are preferable. These organoalkoxysilane may be used singly or as a mixture of two or more.

As the present component (A), use may be made of oligomers and polymers obtained by hydrolyzing part of the alkoxy groups in the aforesaid organoalkoxysilane, followed by intermolecular condensation, hereinafter refer to as a partial hydrolysis and condensation product. The partial hydrolysis and condensation product may be used together with the aforesaid organoalkoxysilane. The partial hydrolysis and condensation may be carried out in the presence of an acid or alkali catalyst.

Component (B) is an aluminum dicarboxylate represented by the following formula (2):

$$(R^3COO)_2Al(OH) \quad (2).$$

In the formula (2), $R^3$ is, independently of each other, a monovalent hydrocarbon group having 1 to 25, preferably 3 to 19 carbon atoms. The monovalent hydrocarbon group is particularly an alkyl group or an alkenyl group. Examples of the monovalent hydrocarbon group include alkyl groups such as a methyl group, an ethyl group, a propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group and a nonadecyl group; and alkenyl groups corresponding to these alkyl groups. $R^3$ may have a linear, cyclic or branched structure. Among these, 1-ethylpentyl group is preferable.

Examples of the aluminum dicarboxylate represented by the aforesaid formula (2) include aluminum soap such as aluminum dioctylate, aluminum distearate, aluminum dilaurate and aluminum dicaprate. The aluminum dicarboxylate may be used singly or as a mixture of two or more.

In particular, $R^3$ in the aforesaid formula (2) is preferably 1-ethylpentyl group and, that is, the aluminum dicarboxylate is aluminum bis(2-ethylhexanoate), i.e. aluminum dioctylate. The component (B) may be a mixture comprising the aluminum bis(2-ethylhexanoate), which is disoap represented by the formula: $(R^4COO)_2Al(OH)$, as a main component and trisoap represented by the formula: $(R^4COO)_3Al$ and monosoap represented by the formula: $(R^4COO)Al(OH)_2$, wherein $R^4COO—$ is 2-ethylhexanoic residue. The total amount of the trisoap and the monosoap is preferably 20 parts by mass or less, relative to total 100 parts by mass of the component (B).

The amount of component (B) is 0.3 to 20 parts by mass, preferably 0.5 to 10 parts by mass, more preferably 1 to 8 parts by mass, relative to 100 parts by mass of component (A). If the amount of component (B) is smaller than the aforesaid lower limit, the composition obtained may not gel or a liquid phase may separate from a gel over time. If the amount of component (B) is larger than the aforesaid upper limit, the gel obtained is too hard and difficult to handle.

Component (C) is an aliphatic acid having 6 to 24 carbon atoms, preferably 6 to 22 carbon atoms. If the number of the carbon atoms is smaller than the aforesaid lower limit, the composition obtained does not gel, or remains in a liquid state with a lower viscosity, or a liquid phase may separate from a gel over time. If the number of the carbon atoms is larger than the aforesaid upper limit, a melting point of the aliphatic acid is too high and, thus, the aliphatic acid needs to be melted at a high temperature before added, which is inconvenient. The aliphatic acid may have a linear, cyclic or branched structure. Further, the aliphatic acid may be saturated or unsaturated.

Examples of the aliphatic acid include caproic acid having 6 carbon atoms, caprylic acid having 8 carbon atoms, 2-ethylhexanoic acid having 8 carbon atoms, capric acid having 10 carbon atoms, lauric acid having 12 carbon atoms, myristic acid having 14 carbon atoms, palmitic acid having 16 carbon atoms, isopalmitic acid having 16 carbon atoms, stearic acid having 18 carbon atoms, isostearic acid having 18 carbon atoms, oleic acid having 18 carbon atoms, linoleic acid having 18 carbon atoms, alpha-linolenic acid having 18 carbon atoms, arachidic acid having 20 carbon atoms, behenic acid having 22 carbon atoms and lignoceric acid having 24 carbon atoms. The aliphatic acid may be used singly or as a mixture of two or more.

Among these, in particular, the aliphatic acid has preferably a linear structure and is further preferably caproic acid having 6 carbon atoms, caprylic acid having 8 carbon atoms, capric acid having 10 carbon atoms, lauric acid having 12 carbon atoms, myristic acid having 14 carbon atoms, palmitic acid having 16 carbon atoms, stearic acid having 18 carbon atoms, oleic acid having 18 carbon atoms, linoleic acid having 18 carbon atoms, alpha-linolenic acid having 18 carbon atoms, arachidic acid having 20 carbon atoms or behenic acid having 22 carbon atoms.

The amount of component (C) is 0.3 to 20 parts by mass, preferably 0.5 to 10 parts by mass, more preferably 0.5 to 8 parts by mass, relative to 100 parts by mass of component (A). If the amount of component (C) is smaller than the aforesaid lower limit, the composition may not gel or a high temperature such as 60 degrees C. or higher and a long time may be needed to make the composition gel. If the amount of component (C) is larger than the aforesaid upper limit, the gel obtained may be too soft or the composition may not gel, but remain in a liquid state.

Component (D) is a dicarboxylic acid having 6 to 30 carbon atoms, preferably 10 to 24 carbon atoms. If the number of the carbon atoms is smaller than the aforesaid lower limit, the composition may not well gel and, that is, the composition may remain in a liquid state with a lower viscosity, a liquid phase may separate from a gel over time, or dicarboxylic acid may not dissolve, but in the gel composition. If the number of the carbon atoms is larger than the aforesaid upper limit, a melting point of the dicarboxylic acid is too high and, thus, the dicarboxylic acid needs to be melted at a high temperature before added, which is inconvenient. The dicarboxylic acid may have a linear, cyclic or branched structure. Further, the dicarboxylic acid may be aliphatic or aromatic, preferably. The aliphatic dicarboxylic acid may be saturated or unsaturated. The dicarboxylic acid may be used singly or as a mixture of two or more.

Examples of the aliphatic dicarboxylic acid include adipic acid having 6 carbon atoms, pimelic acid having 7 carbon atoms, suberic acid having 8 carbon atoms, azelaic acid having 9 carbon atoms, sebacic acid having 10 carbon atoms, dodecanedioic acid having 12 carbon atoms, tetradecanedioic acid having 14 carbon atoms, hexadecanedioic acid having 16 carbon atoms, eicosandioic acid having 20 carbon atoms, 8,13-dimethyl eicosanedioic acid having 22 carbon atoms and 8,13-dimethyl-8,12-eicosadienedioic acid having 22 carbon atoms. Examples of the aromatic dicarboxylic acid include phthalic acid having 8 carbon atoms, isophthalic acid having 8 carbon atoms and terephthalic acid having 8 carbon atoms.

The present dicarboxylic acid includes dicarboxylic acids having a polyorganosiloxane chain, represented by the following formula:

HOOC—X—($R^5_2$SiO)$_t$—$R^5_2$Si—X—COOH wherein t is an integer of 0 or more. t may be a number such that the dicarboxylic acid having a polyorganosiloxane has a weight average molecule weight of 5,000 or less, preferably 3,000 or less. If the weight average molecule weight is larger than the aforesaid upper limit, the present composition may not penetrate well into a substrate, or a surface of a substrate treated with the present composition may have wet color.

In the aforesaid formula, X is a divalent alkylene group having 1 to 10 carbon atoms, such as methylene, ethylene and propylene groups.

In the aforesaid formula, $R^5$ is, independently of each other, a hydrogen atom or a substituted or unsubstituted monovalent hydrocarbon group which has 1 to 10, preferably 1 to 8, carbon atoms and may have an oxygen atom. Examples of the monovalent hydrocarbon group include alkyl groups such as a methyl group, an ethyl group, a propyl group, an isopropyl group, a butyl group, an isobutyl group, a tert-butyl group, a hexyl group, a cyclohexyl group, an octyl group and a decyl group; alkenyl groups such as a vinyl group, an allyl group and an isopropenyl group; aryl groups such as a phenyl group, a xylyl group and a tolyl group; aralkyl groups such as a benzyl group, a phenylethyl group and a phenylpropyl group; and those hydrocarbon groups wherein a part or all of the hydrogen atoms bonded to a carbon atom of these groups are substituted with a halogen atom such as a chlorine atom, a fluorine atom and a bromine atom, such as halogen-substituted monovalent hydrocarbon groups, for instance, chloromethyl, bromoethyl and trifluoropropyl groups. Further, $R^5$ may be a group where some of the hydrogen atoms in an alkyl group is (are) substituted with a polyether group, an amino group, an epoxy group or a carboxyl group, or an organic group having these group.

Any commercial dicarboxylic acid may be used. Examples of the commercial dicarboxylic acid include products manufactured by Okamura oil mill Co., Ltd., such as SL-12 having 12 carbon atoms and SL-20 having 20 carbon atoms, which are linear dibasic acids; such as IPU-22 having 22 carbon atoms, IPS-22 having 22 carbon atoms and SB-20 having 12 to 22 carbon atoms, which are branched dibasic acids; and such as ULB-20 having 20 carbon atoms, which is a mixture of a linear dibasic acid and a branched dibasic acid.

The amount of component (D) is 0.01 to 10 parts by mass, preferably 0.02 to 5 parts by mass, more preferably 0.03 to 3 parts by mass, relative to 100 parts by mass of component (A). If the amount of component (D) is smaller than the aforesaid lower limit, a gel composition obtained is too hard and is not cut easily, so that it would be difficult to scoop up the composition with a spatula or a trowel. Further, the gel is often difficult to be spread thinly and evenly on a surface of a substrate, resulting in an uneven coating. If the amount of component (D) is larger than the aforesaid upper limit, a high temperature such as 60 degrees C. or higher and a longer time may be needed to make the composition gel, or a gel composition obtained returns sometimes to a liquid state over time.

The compositions in the first and second aspects may further comprise (E) a polyorganosiloxane in which dimethylsiloxane units account for 20% or more, preferably 40% or more, of a total number of siloxane units. The component (E) works to improve water repellency of the gel composition.

Examples of the polyorganosiloxane include a compound represented by the following formula (3):

$(R^6_3SiO_{0.5})_p(R^6_2SiO)_q(R^6SiO_{1.5})_r(SiO_2)_s$     (3)

wherein p, r, and s are an integer of 0 or more, q is an integer of 1 or more, a total of p, q, r and s is such that the polyorganosiloxane has a weight average molecular weight of 5,000 or less, preferably 3,000 or less. If the weight average molecule weight is larger than the aforesaid upper limit, the present composition may not penetrate well into a substrate, or a surface of a substrate treated with the present composition may have wet color. In the present invention through the specification, a weight average molecular weight is determined by gel permeation chromatography (GPC) and reduced to polystyrene. The polyorganosiloxane may be used singly or as a mixture of two or more.

In the aforesaid formula (3), $R^6$ is, independently of each other, a hydrogen atom or a substituted or unsubstituted monovalent hydrocarbon group which has 1 to 10, preferably 1 to 8, carbon atoms and may have an oxygen atom. Examples of the monovalent hydrocarbon group include alkyl groups such as a methyl group, an ethyl group, a propyl group, an isopropyl group, a butyl group, an isobutyl group, a tert-butyl group, a hexyl group, a cyclohexyl group, an octyl group and a decyl group; alkenyl groups such as a vinyl group, an allyl group and an isopropenyl group; aryl groups such as a phenyl group, a xylyl group and a tolyl group; aralkyl groups such as a benzyl group, a phenylethyl group and a phenylpropyl group; and those hydrocarbon groups wherein a part or all of the hydrogen atoms in these groups are substituted with a halogen atom such as a chlorine atom, a fluorine atom and a bromine atom, such as halogen-substituted monovalent hydrocarbon groups, for instance, chloromethyl, bromoethyl and trifluoropropyl groups. Further, some of the hydrogen atoms in an alkyl group is (are) substituted with a polyether group, an amino group, an epoxy group or a carboxyl group, or an organic group having these group.

In the aforesaid formula (3), a part of the groups represented by $R^6$ may be an alkoxy group having 1 to 6 carbon atoms, a hydroxyl group or a hydrogen atom. In particular, it is preferred that the aforesaid polyorganosiloxane has an alkoxy group or a hydroxyl group bonded to a silicon atom. Examples of the alkoxy groups include a methoxy group, an ethoxy group, an isopropoxy group, a butoxy group and an isobutoxy group. It is preferred that 40% or more of a total number of $R^6$ in the aforesaid formula (3) is a methyl group. In the present invention, the polyorganosiloxane represented by the aforesaid formula (3) has dimethylsiloxane units represented by the formula $(CH_3)_2SiO$ which accountes for 20% or more, preferably 40% or more, of a total number of a siloxane units represented by the formula $R^6{}_n SiO_{(4-n)/2}$, wherein n is an integer of 0 to 3.

As mentioned above, the polyorganosiloxane represented by the aforesaid formula (3) may have a hydroxyl group or an alkoxy group bonded to a silicon atom. Examples of the siloxane unit include $(R^7O)R^6{}_2SiO_{0.5}$ unit, $(R^7O)R^6SiO$ unit and $(R^7O) SiO_{1.5}$ unit. Examples of $R^7$ include a methyl group, an ethyl group, an isopropyl group, a butyl group, an isobutyl group and a hydrogen atom. In the first aspect, the amount of the hydroxyl group and alkoxy group is, if any, preferably 5 mass % or less, more preferably 3 mass % or less, based on the mass of the polyorganosiloxane. In the second aspect, this amount is, if any, preferably 10 mass % or less, more preferably 7 mass % or less, based on the mass of the polyorganosiloxane. The lower limit of the amount is not particularly limited. If the amount of the hydroxyl group and alkoxy group in the polyorganosiloxane is larger than the aforesaid upper limit, the yield of a gel would be less, which is not preferable.

The amount of component (E) is 0.1 to 50 parts by mass, preferably 0.5 to 30 parts by mass, relative to 100 parts by mass of component (A). If the amount component (E) is larger than the aforesaid upper limit, the composition may not penetrate well into a substrate or a surface, of a substrate treated with the present composition may have wet color.

The compositions in the first and second aspects may further comprise other additives. Any conventional additives which have been used in a water absorption-preventing agent may be used. Examples of the additives include fungicides, algae control agents, ultraviolet absorbing agents, antioxidants, pigments, dyes, thickeners, solvents, waxes and metal soap other than the aforesaid aluminum soap. Further, inorganic fillers such as silica, alumina, titania, mica and talc and an inorganic thickener such as montmorillonite and bentonite may be added. These additives may be properly added according to any conventional manner in such an amount that the effects of the present invention are not obstructed.

The compositions in the first and second aspects may comprise a hydrocarbon, or a paraffin, in order to adjust hardness of the gel. These compounds are preferably have a boiling point or flash point higher than those of the organoalkoxysilane, and a solvent whose boiling point or flash point is lower than that of the organoalkoxysilane is not preferable.

The compositions in the first and second aspects are prepared by mixing the aforesaid components and, thereby, have a gel state. Any conventional methods and equipments may be used for mixing and not limited to any particular ones. For instance, mixers equipped with a paddle type or screw type stirring blades, mixers used in a batch type mixing apparatus such as an anchor mixer, dispermixers, planetary mixers and kneaders; and a mixer used in a continuous mixing apparatus such as a static mixer, a line mixer and a colloid mill are used.

The term "gel" generally means a dispersion which has a high viscosity and no fluidity. The present gel composition is particularly a jelly state.

The mixing temperature may be in a range of from minus 10 degrees C. to a boiling point of the organoalkoxysilane used, but is not limited to these. The temperature may be usually 0 to 80 degrees C., preferably 10 to 70 degrees C. If needed, a mixing may be conducted with heating at 30 to 70 degrees C. to accelerate the gelling.

The compositions in the first and second aspects may be used as a water absorption-preventing agent. By adding the agent on a surface of a porous material, the porous material is made less water-absorptive. Examples of the substrate include inorganic porous materials such as concrete, lightweight concrete, autoclaved lightweight aerated concrete (ALC), mortar, cement plates, plaster boards, calcium silicate plates, bricks, tiles and stones. Further, the substrate may be organic porous materials such as wall mainly made of diatomite, clay or plaster, paper, wood and leather.

An amount of the present composition applied on the substrate is not limited to any particular one and, for instance, may be 5 to 1,000 $g/m^2$. If the amount is smaller than 5 $g/m^2$, the effect to make the substrate less water-absorptive is not sufficient. Even if the amount is more than 1,000 $g/m^2$, a depth of penetration does not become larger anymore and a time period for drying is larger.

Any conventional methods may be used to apply the present composition on the substrate. For instance, brushes, rollers, pallets, trowels and sprays can be used. A desired amount of the present composition can be applied at one time. If needed, the composition may be applied twice or more. Drying after the application may be conducted at room temperature or with heating at 40 to 80 degrees C.

The present inventors believe that the compositions in the first and second aspects gel in the following mechanism. When aluminum bis(2-ethylhexanoate) is added to various kinds of less polar organic solvents, aluminum bis(2-ethylhexanoate) forms a high-molecular weight linear association in the organic solvent, which entangles each other and, the organic solvent is trapped in the between the associations to thereby gels. The present inventors believe that the aluminum dicarboxylate in the present compositions forms associations in the organoalkoxysilane and the organoalkoxysilane is trapped in the between the associations in a similar way as mentioned above. Further, the present inventors believe that the aliphatic acid helps the linear associations formed from the aluminum dicarboxylate to dissolve in the organoalkoxysilane. The composition gels well on account of the combination of the aluminum dicarboxylate and the aliphatic acid added to the organoalkoxysilane. If the composition does not comprise even either one of the aluminum dicarboxylate and the aliphatic acid, the composition does not gel.

Further, the present inventors believe that, in the second aspect of the present invention, the dicarboxylic acid forms cross-linking between parts of the long chains of the associations. Therefore, the gel is prevented from elongating when stretched and easily cracks and cut by pulling and, thus, the gel is easily scooped up from a vessel and applied thinly and evenly with crushing. In contrast, a gel composition which does not comprise the dicarboxylic acid does not crack easily and elongates longer by stretching and, thus, the handling is difficult.

When the present compositions in the first and second aspects are applied to a porous material, the organoalkoxysilane is absorbed into the pores and penetrates deeply through a surface of the material, while maintaining the gel state. Therefore, the composition does not drip after applied and make the porous material less water-absorptive, that is, provides well water repellency to the porous material. The aluminum dicarboxylate has a low polarity and no affinity for water, so that it neither dissolves nor disperses in water. Further, the aliphatic acid also has a low polarity, so that it does not or hardly dissolve in water. Therefore, after the organoalkoxysilane penetrates into the substrate, no component having affinity for water remains on the surface of the substrate and, therefore, very good water absorption-preventing property, i.e. water repellency, is obtained.

EXAMPLES

The present invention will be explained below in further detail with reference to a series of the Examples and the Comparative Examples, though the present invention is in no way limited by these Examples. In the following descriptions, viscosity is determined at 25 degrees C. with a BM type rotary viscometer.

Examples A1 to A14

Compositions of the First Aspect

Example A1

100 Parts by mass of octyltriethoxysilane, 4 parts by mass of Octope Alumi T, i.e., aluminum bis(2-ethylhexanoate) represented by the formula: $(CH_3(CH_2)_3CH(C_2H_5)COO)_2Al(OH)$, ex Hope-Chemical Co., Ltd., and 4 parts by mass of oleic acid were mixed with a planetary mixer at room temperature for about 2 hours to obtain a transparent and colorless gel composition. 50 g of the gel composition was transferred to a 100-milliliter vessel and, then, the vessel was made upside down. The gel composition did not flow out.

Example A2

100 Parts by mass of octyltriethoxysilane, 0.4 part by mass of Octope Alumi T and 0.4 part by mass of oleic acid were mixed with a planetary mixer at 50 degrees C. for about 8 hours to obtain a transparent and colorless gel composition. 50 g of the gel composition was transferred to a 100-milliliter vessel and, then, the vessel was made upside down. The gel composition did not flow out.

Example A3

100 Parts by mass of octyltriethoxysilane, 2.5 parts by mass of Octope Alumi T and 2.5 parts by mass of oleic acid were mixed with a planetary mixer at room temperature for about 2 hours to obtain a transparent and colorless gel composition. 50 g of the gel composition was transferred to a 100-milliliter vessel and, then, the vessel was made upside down. The gel composition did not flow out.

Example A4

100 Parts by mass of octyltriethoxysilane, 2.5 parts by mass of Octope Alumi T and 0.7 part by mass of oleic acid were mixed with a planetary mixer at 50 degrees C. for about 6 hours to obtain a transparent and colorless gel composition. 50 g of the gel composition was transferred to a 100-milliliter vessel and, then, the vessel was made upside down. The gel composition did not flow out.

Example A5

90 Parts by mass of hexyltriethoxysilane, 10 parts by mass of a polydimethylsiloxane represented by the following formula (5):

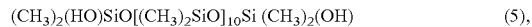

$$(CH_3)_2(HO)SiO[(CH_3)_2SiO]_{10}Si(CH_3)_2(OH) \quad (5),$$

2.5 parts by mass of Octope Alumi T and 2.5 parts by mass of oleic acid were mixed with a planetary mixer at room temperature for about 2 hours to obtain a transparent and colorless gel composition. 50 g of the gel composition was transferred to a 100-milliliter vessel and, then, the vessel was made upside down. The gel composition did not flow out.

Example A6

90 Parts by mass of octyltriethoxysilane, 10 parts by mass of the polydimethylsiloxane represented by the aforesaid formula (5), 2.5 parts by mass of Octope Alumi T and 2.5 parts by mass of oleic acid were mixed with a planetary mixer at room temperature for about 2 hours to obtain a transparent and colorless gel composition. 50 g of the gel composition was transferred to a 100-milliliter vessel and, then, the vessel was made upside down. The gel composition did not flow out.

Example A7

90 Parts by mass of propyltriethoxysilane, 10 parts by mass of the polydimethylsiloxane represented by the aforesaid formula (5), 2.5 parts by mass of Octope Alumi T and 2.5 parts by mass of oleic acid were mixed with a planetary mixer at room temperature for about 2 hours to obtain a transparent and colorless gel composition. 50 g of the gel composition was transferred to a 100-milliliter vessel and, then, the vessel was made upside down. The gel composition did not flow out.

Example A8

90 Parts by mass of methyltriethoxysilane, 10 parts by mass of the polydimethylsiloxane represented by the aforesaid formula (5), 2.5 parts by mass of Octope Alumi T and 2.5 parts by mass of oleic acid were mixed with a planetary mixer at room temperature for about 2 hours to obtain a transparent and colorless gel composition. 50 g of the gel composition was transferred to a 100-milliliter vessel and, then, the vessel was made upside down. The gel composition did not flow out.

Example A9

98 Parts by mass of octyltriethoxysilane, 2 parts by mass of the polydimethylsiloxane represented by the aforesaid formula (5), 2.5 parts by mass of Octope Alumi T and 0.7 part by mass of oleic acid were mixed with a planetary mixer at 50 degrees C. for about 6 hours to obtain a transparent and colorless gel composition. 50 g of the gel composition was transferred to a 100-milliliter vessel and, then, the vessel was made upside down. The gel composition did not flow out.

Example A10

90 Parts by mass of octyltriethoxysilane, 10 parts by mass of the polydimethylsiloxane represented by the aforesaid formula (5), 2.5 parts by mass of Octope Alumi T and 0.7 part by mass of oleic acid were mixed with a planetary mixer at 50 degrees C. for about 6 hours to obtain a transparent and colorless gel composition. 50 g of the gel composition was transferred to a 100-milliliter vessel and, then, the vessel was made upside down. The gel composition did not flow out.

Example A11

90 Parts by mass of hexyltriethoxysilane, 10 parts by mass of the polydimethylsiloxane represented by the aforesaid formula (5), 2.5 parts by mass of Octope Alumi T and 2.5 parts by mass of caproic acid were mixed with a planetary mixer at room temperature for about 2 hours to obtain a transparent and colorless gel composition. 50 g of the gel composition was transferred to a 100-milliliter vessel and, then, the vessel was made upside down. The gel composition did not flow out.

Example A12

90 Parts by mass of hexyltriethoxysilane, 10 parts by mass of the polydimethylsiloxane represented by the aforesaid formula (5), 2.5 parts by mass of Octope Alumi T and 2.5 parts by mass of caprylic acid were mixed with a planetary mixer at room temperature for about 2 hours to obtain a transparent and colorless gel composition. 50 g of the gel composition was transferred to a 100-milliliter vessel and, then, the vessel was made upside down. The gel composition did not flow out.

Example A13

90 Parts by mass of hexyltriethoxysilane, 10 parts by mass of the polydimethylsiloxane represented by the aforesaid formula (5), 2.5 parts by mass of Octope Alumi T and 2.5 parts by mass of stearic acid melted at 80 degrees C. were mixed with a planetary mixer at 50 degrees C. for about 2 hours to obtain a transparent and colorless gel composition. 50 g of the gel composition was transferred to a 100-milliliter vessel and, then, the vessel was made upside down. The gel composition did not flow out.

Example A14

90 Parts by mass of hexyltriethoxysilane, 10 parts by mass of the polydimethylsiloxane represented by the aforesaid formula (5), 2.5 parts by mass of Octope Alumi T and 2.5 parts by mass of behenic acid melted at 80 degrees C. were mixed with a planetary mixer at 50 degrees C. for about 2 hours to obtain a transparent and colorless gel composition. 50 g of the gel composition was transferred to a 100-milliliter vessel and, then, the vessel was made upside down. The gel composition did not flow out.

Comparative Example 1

100 Parts by mass of hexyltriethoxysilane, 0.2 part by mass of Octope Alumi T and 0.2 part by mass of oleic acid were mixed with a planetary mixer at 50 degrees C. for about 8 hours. The resulting product remained in a liquid state and did not gel.

Comparative Example 2

100 Parts by mass of hexyltriethoxysilane and 2.5 parts by mass of Octope Alumi T were mixed with a planetary mixer at 50 degrees C. for about 8 hours. The resulting product remained in a liquid state and did not gel.

Comparative Example 3

100 Parts by mass of hexyltriethoxysilane and 2.5 parts by mass of oleic acid were mixed with a planetary mixer at 50 degrees C. for about 8 hours. The resulting product remained in a liquid state and did not gel.

Comparative Example 4

90 Parts by mass of hexyltriethoxysilane, 10 parts by mass of the polydimethylsiloxane represented by the aforesaid formula (5), 2.5 parts by mass of Octope Alumi T and 2.5 parts by mass of butyric acid were mixed with a planetary mixer at room temperature for about 2 hours, during which viscosity of the mixture increased. However, after two days, the mixture returned to a liquid state and, thus, a stable gel was not obtained.

Comparative Example 5

8.5 Parts by mass of a polydimethylsiloxane which has a viscosity of 1,600 mPa·s, an N-(2-aminoethyl)-3-aminopropyl group in the side chain and an amine equivalent of 10,000 g/eq, 0.14 part by mass of a nonionic surfactant, EMULGEN 104P, ex Kao Corporation, 0.79 part by mass of a nonionic surfactant, EMULGEN 123P, ex Kao Corporation, and 4.6 parts by mass of water were mixed with a homomixer to emulsify. 76.5 Parts by mass of hexyltriethoxysilane was gradually added to the emulsion, while mixing with the homomixer. After the whole amount of hexyltriethoxysilane was added, the mixture was further mixed with a dispermixer. Subsequently, 9.5 parts by mass of water was added to dilute the mixture to thereby obtain a white creamy emulsion having a viscosity of 100,000 mPa·s or more and comprising 85 mass % of silicone components. When this emulsion composition was applied on a surface of a test piece, remarkable dripping took place so that a part of the composition flowed away at the side face.

Comparative Example 6

100 Parts by mass of hexyltriethoxysilane, 6 parts by mass of a polydimethylsiloxane which has a viscosity of 3,700 mPa·s, an N-(2-aminoethyl)-3-aminopropyl group in the side chain and an amine equivalent of 2,000 g/eq and 12 parts by mass of hydrophobic fumed silica, AEROSIL R812, ex Nippon Aerosil Co., Ltd., were mixed with a dispermixer at room temperature for about 10 minutes to obtain homogeneous paste. When this paste composition was applied on a surface of a test piece, appearance of the surface became white due to the silica present on the surface.

Regarding the compositions obtained in Examples A1 to A14 and Comparative Examples 5 and 6, dripping, appearance, water repellency and a depth of penetration of the composition were evaluated in the manners described below. The results are as shown in Tables 1 to 4. The compositions obtained in Comparative Examples 1 to 3 did not gel so that these compositions were not subjected to the evaluation tests. Further, the gel condition of the composition obtained in Comparative Example 4 was not stable so that the composition was not subjected to the evaluation tests either.

(1) Dripping

A mortar test piece having 70 mm length, 70 mm width and 25 mm height, was used, which had been prepared according to the Japanese Industrial Standards (JIS) R 5201. Each of the composition was applied in an amount of 200 g/m² on a face having 70 mm length and 70 mm width of the mortar test piece, and spread evenly with a spatula. Immediately after the spreading, the test piece was left standing with the coated face being vertical. A visual inspection was conducted to confirm whether the composition flowed down to spread or not.

(2) Appearance

The composition was applied on the mortar test piece in the same manner as in (1) above. The test piece was left standing for seven days at 25 degrees C. and a 50% relative humidity to be aged. Then, an area of surface parts having wet color was assessed by a visual inspection and scored according to the following criteria.

5: An area of surface parts having wet color was 5% or less, relative to the whole area coated with the composition, that is, the test piece had appearance equal to a test piece on which the composition was not applied.

4: An area of surface parts having wet color was more than 5% to less than 25%, relative to the whole area coated with the composition.

3: An area of surface parts having wet color was 25% or more to less than 75%, relative to the whole area coated with the composition.

2: An area of surface parts having wet color was 75% or more to less than 95%, relative to the whole area coated with the composition.

2: An area of surface parts having wet color was 95% or more, relative to the whole area coated with the composition.

(3) Water Repellency

The composition was applied on the mortar test piece in the same manner as in (1) above. The test piece was left standing for seven days at 25 degrees C. and a 50% relative humidity to be aged. Then, water was applied on the face coated with the composition with a shower for 5 minutes. An area of surface parts which repelled water, and an area of surface parts which had wet color were assessed by a visual inspection and scored according to the following criteria.

[Water Repellency]

5: An area of surface parts repelling water was 95% or more, relative to the whole area coated with the composition.

4: An area of surface parts repelling water was 75% or more to less than 95%, relative to the whole area coated with the composition.

3: An area of surface parts repelling water was 25% or more to less than 75%, relative to the whole area coated with the composition.

2: An area of surface parts repelling water was 5% or more to less than 25%, relative to the whole area coated with the composition.

1: An area of surface parts repelling water was less than 5%, relative to the whole area coated with the composition.

[Wet Color]

5: An area of surface parts having wet color was 5% or less, relative to the whole area coated with the composition.

4: An area of surface parts having wet color was more than 5% to less than 25%, relative to the whole area coated with the composition.

3: An area of surface parts having wet color was 25% or more to less than 75%, relative to the whole area coated with the composition.

2: An area of surface parts having wet color was 75% or more to less than 95%, relative to the whole area coated with the composition.

1: An area of surface parts having wet color was 95% or more, relative to the whole area coated with the composition.

(4) Depth of Penetration

The composition was applied on the mortar test piece in the same manner as in (1) above. The test piece was left standing for seven days at 25 degrees C. and a 50% relative humidity to be aged. The test piece was cut vertically to the face coated with the composition and water was sprayed on the cut surface. A depth of a part which neither absorbed water nor colored with water was measured.

TABLE 1

| | | | Example A | | | | | | | | | |
|---|---|---|---|---|---|---|---|---|---|---|---|---|
| | | | 1 | 2 | 3 | 4 | 5 | 6 | 7 | 8 | 9 | 10 |
| Component, part by mass | (A) | Hexyltriethoxysilane | | | 100 | | 90 | | | | | |
| | | Octyltriethoxysilane | 100 | 100 | | 100 | | 90 | | | 98 | 90 |
| | | Propyltriethoxysilane | | | | | | | 90 | | | |
| | | Methyltriethoxysilane | | | | | | | | 90 | | |
| | (B) | Octope Alumi T | 4 | 0.4 | 2.5 | 2.5 | 2.5 | 2.5 | 2.5 | 2.5 | 2.5 | 2.5 |
| | (C) | Oleic acid | 4 | 0.4 | 2.5 | 0.7 | 2.5 | 2.5 | 2.5 | 2.5 | 0.7 | 0.7 |
| | (E) | Polydimethylsiloxane | | | | | 10 | 10 | 10 | 10 | 2 | 10 |
| Evaluation | (1) | Dripping | No | No | No | No | No | No | No | No | No | No |
| | (2) | Appearance | 5 | 5 | 5 | 5 | 5 | 5 | 5 | 5 | 5 | 5 |
| | (3) | Water repellency | 5 | 5 | 5 | 5 | 5 | 5 | 5 | 5 | 5 | 5 |
| | | Wet color | 5 | 5 | 5 | 5 | 5 | 5 | 5 | 5 | 5 | 5 |
| | (4) | Depth of penetration, mm | 9.1 | 8.2 | 9.4 | 7.8 | 8.8 | 7.9 | 8.3 | 6.1 | 7.8 | 7.5 |

TABLE 2

| | | | Comparative Example | | |
|---|---|---|---|---|---|
| | | | 1 | 2 | 3 |
| Component, part by mass | (A) | Hexyltriethoxysilane | 100 | 100 | 100 |
| | | Octyltriethoxysilane | | | |
| | | Propyltriethoxysilane | | | |
| | | Methyltriethoxysilane | | | |
| | (B) | Octope Alumi T | | 0.2 | 2.5 |
| | (C) | Oleic acid | | 0.2 | 2.5 |
| | (E) | Polydimethylsiloxane | | | |
| Evaluation | (1) | Dripping | Not gelled. | Not gelled. | Not gelled. |
| | (2) | Appearance | | | |
| | (3) | Water repellency | | | |
| | | Wet color | | | |
| | (4) | Depth of penetration, mm | | | |

TABLE 3

| | | | Example A | | | | Comparative Example |
|---|---|---|---|---|---|---|---|
| | | | 11 | 12 | 13 | 14 | 4 |
| Component, part by mass | (A) | Hexyltriethoxysilane | 90 | 90 | 90 | 90 | 90 |
| | (B) | Octope Alumi T | 2.5 | 2.5 | 2.5 | 2.5 | 2.5 |
| | (C) | Caproic acid having 6 carbon | 2.5 | | | | |
| | | Caprylic acid having 8 carbon | | 2.5 | | | |
| | | Stearic acid having 18 carbon | | | 2.5 | | |
| | | Behenic acid having 22 carbon | | | | 2.5 | |
| | | Butyric acid having 4 carbon | | | | | 2.5 |
| | (E) | Polydimethylsiloxane | 10 | 10 | 10 | 10 | 10 |
| Evaluation | (1) | Dripping | No | No | No | No | Not gelled. |
| | (2) | Appearance | 5 | 5 | 5 | 5 | |
| | (3) | Water repellency | 5 | 5 | 5 | 5 | |
| | | Wet color | 5 | 5 | 5 | 5 | |
| | (4) | Depth of penetration, mm | 7.7 | 8 | 7.8 | 7.4 | |

TABLE 4

| | | Comparative Example | |
|---|---|---|---|
| | | 5 | 6 |
| | Conventional water-absorption inhibitor | Creamy emulsion composition | Paste compostion comprising silica |
| Evaluation | (1) Dripping | Flowed down. | No |
| | (2) Appearance | 5 | White |
| | (3) Water repellency | 1 | 5 |
| | Wet color | 2 | 5 |
| | (4) Depth of penetration, mm | 7.4 | 6.7 |

As shown in Tables 1 and 3, the organoalkoxysilane gelled well on account of the combination of the aluminum dicarboxylate and the specific aliphatic acid added to the organoalkoxysilane. In contrast, as shown in Table 2, when either one of the aluminum dicarboxylate and the aliphatic acid was not added, the organoalkoxysilane did not gel well. Further, as shown in Tables 1 and 3, even when the present gel composition was applied on the vertical surface of the porous material, the gel composition did not drip, and provided good appearance, penetrated deeply from the surface of the porous material to make the porous material less water-absorptive, that is, to provide good water repellency to the porous material.

Examples B1 to B10

Compositions of the Second Aspect

Example B1

90 Parts by mass of octyltriethoxysilane, 10 parts by mass of polydimethylsiloxane represented by the following formula (5):

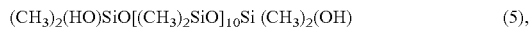

$$(CH_3)_2(HO)SiO[(CH_3)_2SiO]_{10}Si(CH_3)_2(OH) \quad (5),$$

2.5 parts by mass of Octope Alumi T, i.e. aluminum bis(2-ethylhexanoate) represented by the formula: $(CH_3(CH_2)_3CH(C_2H_5)COO)_2Al(OH)$, ex Hope-Chemical Co., Ltd., 2.5 parts by mass of oleic acid and 0.1 part by mass of adipic acid were mixed with a planetary mixer at 50 degrees C. for about 4 hours to obtain a transparent and colorless gel composition. 50 g of the gel composition was transferred to a 100-milliliter vessel and, then, the vessel was made upside down. The gel composition did not flow out.

Example B2

90 Parts by mass of octyltriethoxysilane, 10 parts by mass of polydimethylsiloxane represented by the aforesaid formula (5), 2.5 parts by mass of Octope Alumi T, 2.5 parts by mass of oleic acid and 0.1 part by mass of sebacic acid were mixed with a planetary mixer at 50 degrees C. for about 4 hours to obtain a transparent and colorless gel composition. 50 g of the gel composition was transferred to a 100-milliliter vessel and, then, the vessel was made upside down. The gel composition did not flow out.

Example B3

90 Parts by mass of octyltriethoxysilane, 10 parts by mass of polydimethylsiloxane represented by the aforesaid formula (5), 2.5 parts by mass of Octope Alumi T, 2.5 parts by mass of oleic acid and 0.1 part by mass of dicarboxylic acid SB20, i.e., branched dibasic acid having 12 to 22 carbon atoms, ex Okamura Oil Mill Co., Ltd., were mixed with a planetary mixer at 50 degrees C. for about 4 hours to obtain a transparent and colorless gel composition. 50 g of the gel composition was transferred to a 100-milliliter vessel and, then, the vessel was made upside down. The gel composition did not flow out.

Example B4

90 Parts by mass of octyltriethoxysilane, 10 parts by mass of polydimethylsiloxane represented by the aforesaid formula (5), 2.5 parts by mass of Octope Alumi T, 2.5 parts by mass of oleic acid and 0.1 part by mass of dicarboxylic acid IPS22, i.e., branched dibasic acid having 22 carbon atoms, ex Okamura Oil Mill Co., Ltd., were mixed with a planetary mixer at 50 degrees C. for about 4 hours to obtain a transparent and colorless gel composition. 50 g of the gel composition was transferred to a 100-milliliter vessel and, then, the vessel was made upside down. The gel composition did not flow out.

Example B5

90 Parts by mass of octyltriethoxysilane, 10 parts by mass of polydimethylsiloxane represented by the aforesaid formula (5), 2.5 parts by mass of Octope Alumi T, 2.5 parts by mass of oleic acid and 0.1 part by mass of dicarboxylic acid IPU22, i.e., branched dibasic acid having 22 carbon atoms, ex Okamura Oil Mill Co., Ltd., were mixed with a planetary mixer at 50 degrees C. for about 4 hours to obtain a transparent and colorless gel composition. 50 g of the gel composition was transferred to a 100-milliliter vessel and, then, the vessel was made upside down. The gel composition did not flow out.

Example B6

90 Parts by mass of octyltriethoxysilane, 10 parts by mass of polydimethylsiloxane represented by the aforesaid formula (5), 2.5 parts by mass of Octope Alumi T, 1.0 part by mass of oleic acid and 0.05 part by mass of dicarboxylic acid IPU22 were mixed with a planetary mixer at 50 degrees C. for about 4 hours to obtain a transparent and colorless gel composition. 50 g of the gel composition was transferred to a 100-milliliter vessel and, then, the vessel was made upside down. The gel composition did not flow out.

Example B7

97 Parts by mass of octyltriethoxysilane, 3 parts by mass of polydimethylsiloxane represented by the aforesaid formula (5), 2.5 parts by mass of Octope Alumi T, 2.5 parts by mass of oleic acid and 0.1 part by mass of dicarboxylic acid IPU22 were mixed with a planetary mixer at 50 degrees C. for about 4 hours to obtain a transparent and colorless gel composition. 50 g of the gel composition was transferred to a 100-milliliter vessel and, then, the vessel was made upside down. The gel composition did not flow out.

Example B8

97 Parts by mass of octyltriethoxysilane, 3 parts by mass of polydimethylsiloxane represented by the aforesaid formula (5), 2.5 parts by mass of Octope Alumi T, 1.0 part by mass of oleic acid and 0.05 part by mass of dicarboxylic acid IPU22 were mixed with a planetary mixer at 50 degrees C. for about 4 hours to obtain a transparent and colorless gel composition. 50 g of the gel composition was transferred to a 100-milliliter vessel and, then, the vessel was made upside down. The gel composition did not flow out.

Example B9

100 Parts by mass of octyltriethoxysilane, 2.5 parts by mass of Octope Alumi T, 2.5 parts by mass of oleic acid and 0.1 part by mass of dicarboxylic acid IPU22 were mixed with a planetary mixer at 50 degrees C. for about 4 hours to obtain a transparent and colorless gel composition. 50 g of the gel composition was transferred to a 100-milliliter vessel and, then, the vessel was made upside down. The gel composition did not flow out.

Example B10

100 Parts by mass of octyltriethoxysilane, 2.5 parts by mass of Octope Alumi T, 1.0 part by mass of oleic acid and 0.05 part by mass of dicarboxylic acid IPU22 were mixed with a planetary mixer at 50 degrees C. for about 4 hours to obtain a transparent and colorless gel composition. 50 g of the gel composition was transferred to a 100-milliliter vessel and, then, the vessel was made upside down. The gel composition did not flow out.

The compositions prepared in the following Examples C1 to C3 are according to the first aspect of the present invention.

Example C1

90 Parts by mass of octyltriethoxysilane, 10 parts by mass of polydimethylsiloxane represented by the aforesaid formula (5), 2.5 parts by mass of Octope Alumi T and 2.5 parts by mass of oleic acid were mixed with a planetary mixer at 50 degrees C. for about 4 hours to obtain a transparent and colorless gel composition. 50 g of the gel composition was transferred to a 100-milliliter vessel and, then, the vessel was made upside down. The gel composition did not flow out.

Example C2

97 Parts by mass of octyltriethoxysilane, 3 parts by mass of polydimethylsiloxane represented by the aforesaid formula (5), 2.5 parts by mass of Octope Alumi T and 2.5 parts by mass of oleic acid were mixed with a planetary mixer at 50 degrees C. for about 4 hours to obtain a transparent and colorless gel composition. 50 g of the gel composition was transferred to a 100-milliliter vessel and, then, the vessel was made upside down. The gel composition did not flow out.

Example C3

100 Parts by mass of octyltriethoxysilane, 2.5 parts by mass of Octope Alumi T and 2.5 parts by mass of oleic acid were mixed with a planetary mixer at 50 degrees C. for about 4 hours to obtain a transparent and colorless gel composition. 50 g of the gel composition was transferred to a 100-milliliter vessel and, then, the vessel was made upside down. The gel composition did not flow out.

In the following Comparative Example 7, a dicarboxylic acid having four carbon atoms, i.e. succinic acid, was used.

Comparative Example 7

100 Parts by mass of octyltriethoxysilane, 2.5 parts by mass of Octope Alumi T, 2.5 parts by mass of oleic acid and 0.1 part by mass of succinic acid were mixed with a planetary mixer at 50 degrees C. for about 4 hours. The resulting product remained in a liquid state and did not gel.

In the following evaluation tests, it was confirmed that the gel compositions of the present second aspect showed the improved cutting property (as explained below) and spreadability in addition to the same effects as in the first aspect compositions.

For the compositions obtained in Examples B1 to B10 and C1 to C3, (1) dripping, (2) appearance, (3) water repellency and (4) depth of penetration were evaluated in the aforesaid manners. Additionally, (5) cutting property and spreadability and (6) cracks in gel were evaluated in the manners described below. The results are as shown in Table 5.

(5) Cutting Property and Spreadability

The gel composition was scooped up from the vessel with a spatula. When the composition cut to remain on a head of the spatula, it was evaluated as "good". In contrast, when the composition elongated and did not cut and, thus, did not remain on the head of the spatula, it was evaluated as "bad".

Further, the composition was applied on the mortar test piece in the same manner as in (1) above. The composition which spread evenly was evaluated as "good". In contrast, when part of the composition agglomerated partially not to spread evenly, it was evaluated as "bad".

(6) Cracks in Gel 30 g of the gel composition was transferred to a plastic vessel having an inner diameter of about 37 mm and a depth of about 50 mm, left standing for a one day at room temperature to be defoamed and to make the surface flat. A cylindrical probe having a diameter of 12.7 mm and a length of 35 mm was push down with a texture analyzer, CT3-1000, ex Brookfield, at an insertion rate of 5 mm/second for 5 seconds to a depth of 25 mm from the surface of the gel, stopped for 5 seconds and, then, pulled up at 5 mm/second for 5 seconds. When the gel cracked, it was evaluated as "good". In contrast, when the gel did not crack and returned to the initial state, it was evaluated as "bad".

Figure 2:
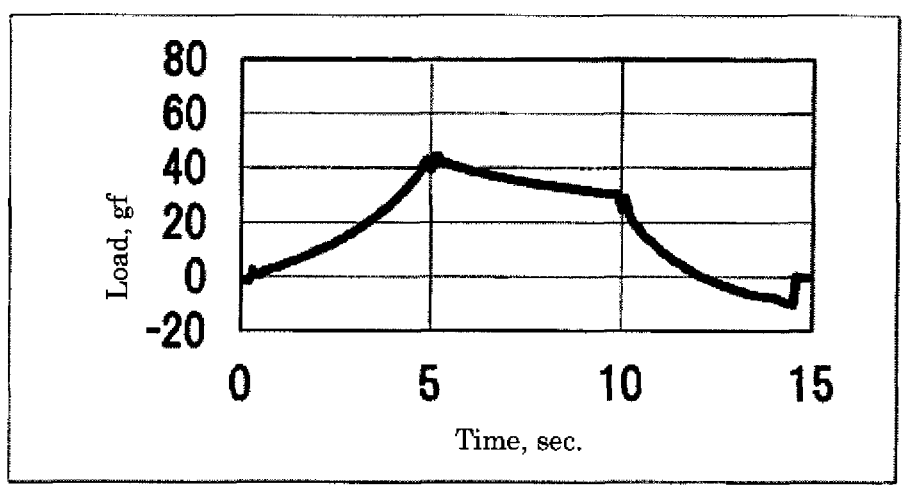
FIG. 2 is a load curve of the gel obtained in Example C3.

In the aforesaid test (6), change of load applied on the gels of Example B10 and Example C3 was monitored as seen in FIGS. 1 and 2, respectively. FIG. 1 indicates that the load curve changed abruptly after about 4 seconds. This means that the gel cracked. FIG. 2 indicates that the load curve changed smoothly in the first 5 seconds for the insertion. This means that the gel did not crack.

the composition in the present second aspect has a good workability of the gel in applying it evenly on a surface of porous materials. Therefore, the present compositions are particularly useful as an agent for making architectural or civil engineering inorganic porous materials less water-absorptive.

The invention claimed is:

1. A composition comprising
   (A) 100 parts by mass of an organoalkoxysilane represented by the following formula (1) and/or a compound obtained by partial hydrolysis and condensation of said organoalkoxysilane,

TABLE 5

| | | | Example B | | | | | | | | | | Example C | | | Comparative Example |
|---|---|---|---|---|---|---|---|---|---|---|---|---|---|---|---|---|
| | | | 1 | 2 | 3 | 4 | 5 | 6 | 7 | 8 | 9 | 10 | 1 | 2 | 3 | 7 |
| Component, part by mass | (A) | Octyltriethoxysilane | 90 | 90 | 90 | 90 | 90 | 90 | 97 | 97 | 100 | 100 | 90 | 97 | 100 | 100 |
| | (B) | Octope Alumi T | 2.5 | 2.5 | 2.5 | 2.5 | 2.5 | 2.5 | 2.5 | 2.5 | 2.5 | 2.5 | 2.5 | 2.5 | 2.5 | 2.5 |
| | (C) | Oleic acid | 2.5 | 2.5 | 2.5 | 2.5 | 2.5 | 1 | 2.5 | 1 | 2.5 | 1 | 2.5 | 2.5 | 2.5 | 2.5 |
| | (D) | Adipic acid having 6 carbon atoms | 0.1 | | | | | | | | | | | | | |
| | | Sebacic acid having 10 carbon atoms | | 0.1 | | | | | | | | | | | | |
| | | SB20 having 12 to 22 carbon atoms | | | 0.1 | | | | | | | | | | | |
| | | IPS22 having 22 carbon atoms | | | | 0.1 | | | | | | | | | | |
| | | IPU22 having 22 carbon atoms | | | | | 0.1 | 0.05 | 0.1 | 0.05 | 0.1 | 0.05 | | | | |
| | | Succinic acid having 4 carbon atoms | | | | | | | | | | | | | | 0.1 |
| | (E) | Polydimethylsiloxane | 10 | 10 | 10 | 10 | 10 | 10 | 3 | 3 | | | 10 | 3 | | |
| Evaluation | (1) | Dripping | No | No | No | No | No | No | No | No | No | No | No | No | No | Not gelled. |
| | (2) | Appearance | 5 | 5 | 5 | 5 | 5 | 5 | 5 | 5 | 5 | 5 | 5 | 5 | 5 | |
| | (3) | Water repellency | 5 | 5 | 5 | 5 | 5 | 5 | 5 | 5 | 5 | 5 | 5 | 5 | 5 | |
| | | Wet color | 5 | 5 | 5 | 5 | 5 | 5 | 5 | 5 | 5 | 5 | 5 | 5 | 5 | |
| | (4) | Depth of penetration, mm | 7.1 | 7.2 | 7.4 | 7.9 | 7.6 | 7.7 | 7.3 | 7.7 | 7.4 | 7.7 | 7.8 | 7.7 | 7.8 | |
| | (5) | Cutting property | Good | Good | Good | Good | Good | Good | Good | Good | Good | Good | Bad | Bad | Bad | |
| | | Spreadability | Good | Good | Good | Good | Good | Good | Good | Good | Good | Good | Bad | Bad | Bad | |
| | (6) | Cracks in gel | Good | Good | Good | Good | Good | Good | Good | Good | Good | Good | Bad | Bad | Bad | |

As shown in Table 5, the gel composition of the present second aspect did not drip even when it was applied on the vertical face, provided a good appearance to the surface of the porous material, penetrated deeply from the surface of the porous material and made the porous material less water-absorptive, that is, to provide good water repellency to the porous material. Further, the gel composition cracked and cut easily to have a good spreadability. That is, the gel of the present second aspect has the same effects as in the present first aspect and, additionally, has a good workability to be applied on the surface of porous materials. In contrast, the gel compositions comprising no dicarboxylic acid did not crack and cut easily and had a poor spreadability.

INDUSTRIAL APPLICABILITY

The present compositions do not drip even when they are applied on a vertical face of porous materials, provide a good appearance, penetrate deeply from the surface and make porous materials less water-absorptive. Additionally, the present compositions can be used in a form of a solventless gel composition which comprises substantially neither water nor organic solvent. When the solventless gel composition is applied on a substrate, VOCs, i.e. volatility organic compounds, due to an organic solvent does not evaporate. Further,

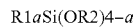

wherein R1 is, independently of each other, a monovalent hydrocarbon group having 1 to 20 carbon atoms, R2 is, independently of each other, a monovalent hydrocarbon group having 1 to 8 carbon atoms and a is an integer of 1, 2 or 3, (B) 0.3 to 20 parts by mass of an aluminum dicarboxylate represented by the following formula (2):

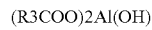

wherein R3 is, independently of each other, a monovalent hydrocarbon group having 1 to 25 carbon atoms, and (C) 0.3 to 20 parts by mass of an aliphatic acid having 6 to 24 carbon atoms.

2. A composition comprising
   (A) 100 parts by mass of an organoalkoxysilane represented by the following formula (1) and/or a compound obtained by partial hydrolysis and condensation of said organoalkoxysilane,

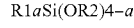

wherein R1 is, independently of each other, a monovalent hydrocarbon group having 1 to 20 carbon atoms, R2 is, independently of each other, a monovalent hydrocarbon group having 1 to 8 carbon atoms and a is an integer of 1, 2 or 3, (B) 0.3 to 20 parts by mass of an aluminum dicarboxylate represented by the following formula (2):

$$(R3COO)2Al(OH) \quad (2)$$

wherein R3 is, independently of each other, a monovalent hydrocarbon group having 1 to 25 carbon atoms, (C) 0.3 to 20 parts by mass of an aliphatic acid having 6 to 24 carbon atoms, and (D) 0.01 to 10 parts by mass of a dicarboxylic acid having 6 to 30 carbon atoms.

3. The composition according to claim 1, further comprising (E) a polyorganosiloxane wherein dimethylsiloxane units account for 20% or more of a total number of siloxane units, in an amount of 0.1 to 50 parts by mass, relative to 100 parts by mass of component (A).

4. The composition according to claim 1 comprising substantially neither water nor organic solvent.

5. A method for making a porous material less water-absorptive by applying the composition according to claim 1 to a surface of said porous material.

6. The method according to claim 5, wherein said porous material is inorganic.

7. A porous material modified by said method according to claim 5.

* * * * *